United States Patent [19]

Yoneyama et al.

[11] Patent Number: 5,362,482
[45] Date of Patent: Nov. 8, 1994

[54] WATER-IN-OIL EMULSION SOLID COSMETIC COMPOSITION

[75] Inventors: Toshio Yoneyama; Yasuo Matsuoka; Harumi Suzuki; Shigenori Kumagai; Susumu Takada, all of Yokohama, Japan

[73] Assignee: Shiseido Company Ltd., Tokyo, Japan

[21] Appl. No.: 16,673

[22] Filed: Feb. 10, 1993

Related U.S. Application Data

[63] Continuation of Ser. No. 442,812, Nov. 28, 1989, abandoned, which is a continuation-in-part of Ser. No. 287,784, Dec. 20, 1988, abandoned.

[51] Int. Cl.⁵ .................... A61K 7/021; A61K 7/035
[52] U.S. Cl. ........................................ 424/69; 424/63; 424/403; 424/404; 424/405; 424/406; 424/407; 514/63; 514/69; 514/937; 514/941; 514/938; 514/844; 514/845; 514/846; 514/847; 514/848; 523/209; 523/213; 523/215; 523/216
[58] Field of Search ........... 424/61, 63, 69, 64, 424/401, 78, 403–407; 514/63, 937, 69, 941, 938, 844–848; 523/209, 213, 215, 216

[56] References Cited

U.S. PATENT DOCUMENTS

| | | | |
|---|---|---|---|
| 4,268,499 | 5/1981 | Keil | 514/941 |
| 4,374,825 | 2/1983 | Bolich, Jr. et al. | 424/70 |
| 4,387,090 | 6/1983 | Bolich, Jr. | 424/70 |
| 4,675,179 | 6/1987 | Suzuki et al. | 514/941 |
| 4,698,178 | 10/1987 | Huttinger et al. | 252/309 |
| 4,801,445 | 1/1989 | Fukui et al. | 424/69 |
| 4,818,614 | 4/1989 | Fukui | 424/63 |

FOREIGN PATENT DOCUMENTS

| | | | |
|---|---|---|---|
| 0152953 | 8/1982 | European Pat. Off. | |
| 0076146 | 6/1983 | European Pat. Off. | |
| 0271925 | 6/1988 | European Pat. Off. | |
| 0251679 | 7/1988 | European Pat. Off. | |
| 56-16404 | 2/1981 | Japan | 424/69 |
| 60-126209 | 5/1985 | Japan | 424/63 |
| 60-197610 | 7/1985 | Japan | |
| 61-113646 | 5/1986 | Japan | 424/63 |
| 61-114721 | 6/1986 | Japan | 424/63 |
| 2155337 | 9/1985 | United Kingdom | 514/63 |

*Primary Examiner*—F. T. Moezie
*Attorney, Agent, or Firm*—Sprung Horn Kramer & Woods

[57] ABSTRACT

A water-in-oil type emulsified solid composition containing (a) an oil component such as a silicone oil, (b) a solid wax and/or an oil-gelling agent, (c) water, and (d) (i) a polyoxyalkylene modified organopolysiloxane or (ii) a lipophilic surfactant and a hydrophobically treated powder, wherein the water content is 5% by weight or more, based upon the total amount of the composition.

9 Claims, No Drawings

WATER-IN-OIL EMULSION SOLID COSMETIC COMPOSITION

CROSSREFERENCE TO RELATED APPLICATION

This application is a continuation, of application Ser. No. 442,812, filed Nov. 28, 1989, which in turn is a continuation-in-part of Ser. No. 287,784, filed Dec. 20, 1988, both are now abandoned.

BACKGROUND OF THE INVENTION

1. Field of the Invention

The present invention relates to a water-in-oil type emulsified cosmetic composition containing, as essential constituents, an oil component such as a silicone oil, a solid wax and/or an oil-gelling agent, water, and polyoxyalkylene modified organopolysiloxane or a lipophilic surfactant and a hydrophobically treated powder. More specifically, it relates to a water-in-oil emulsion type solid cosmetic composition having an excellent stability, prolonged cosmetic finish and a novel feeling when applied, i.e., providing a cool and refreshing feeling when applied to the skin even in the form of a solid.

2. Description of the Related Art

As the base types generally used for solid cosmetic compositions, solid oily types obtained by solidifying oil, solid pressed types obtained by pressing powder, or mixtures of powder and oily agents, and the like are known. These base types are properly used depending upon the purposes and methods of use of the cosmetic composition. For example, solid oily types are usually used for stick type cosmetics such as lipsticks, and solid pressing types are usually used for a foundation applied with a puff or sponge. Recently, lipsticks containing water formulated therein have been developed and are available on the market, but since it is to obtain such lipsticks having a good stability and good cosmetic finish durability, the amount of water formulated is small and, therefore, there is little difference in the application feeling thereof when compared to conventional solid oily types. Furthermore, the oily type cosmetic products containing water and powder have disadvantages such that the stability becomes suddenly poor or the cosmetic finish durability becomes poor, when the kinds of powder are changed. Particularly, when volatile oily agents are used, it is difficult to obtain lipsticks having a good stability, and further, such lipsticks must be filled in containers having high sealing properties. Therefore, because of the above-mentioned limitations, lipsticks containing water therein are not popular in the market. Namely, water-in-oil emulsion type solid cosmetics having a good stability were not available heretofore, and furthermore, water-in-oil emulsion type solid cosmetics containing a large amount of water together with a volatile oily agent are not known in the art, because of the difficulty of a good stability and cosmetic finish durability.

On the other hand, emulsified type cosmetics are widely used as basic cosmetic because water and humectants can be formulated therein and excellent treatment properties can be obtained. In the case of the emulsion type cosmetics, only the fluidizable emulsified type or the less fluidizable cream type are available, and therefore, the forms of the containers in which they are to be filled are limited due to the fluidity of these cosmetics. Namely, the containers are limited to bottle or tubes in the case of the cream type, and to bottles in the case of the emulsion type. Also, the emulsified type cosmetics have a poor portability, although the effects on the skin are excellent.

Recently, cosmetics using silicone oil as a water repellent base agent have been extensively studied. This is because, since silicone oil has excellent water repellent properties, the coated film of cosmetics after application is has a strong resistance to water and sweat (or perspiration) and has a good adherence to the skin, and therefore, silicone oil is utilized in, for example, oily solid type cosmetics in which the oil phase is a continuous phase, and water-in-oil type emulsion or cream cosmetics.

Further, the formulation of volatile oily agents has been studied. This formulation is intended to suppress the clinging to the skin feeling caused by the use of conventional oils, which is a drawback of oily solid type cosmetics and water-in-oil type cream cosmetics, by volatilizing the volatile oil after application to the skin. But emulsified solid cosmetics containing silicone oil formulated therein are not known, because the stability of the resultant cosmetics is poor when silicone oil, especially volatile silicone oil, is formulated.

Furthermore, recently the use of a volatile oil in cosmetic has been studied, but the problems of stability, especially a good feeling (e.g., cool and refreshing feeling) when applied, and a good cosmetic finish durability is difficult to obtain with solid type cosmetic compositions, although relatively stable emulsion or cream type cosmetic compositions are available.

SUMMARY OF THE INVENTION

Accordingly, the objects of the present invention are to eliminate the above-mentioned disadvantages of the prior art and to provide an emulsified solid cosmetic composition containing an oil component such as silicone oil and having an excellent stability and good feeling upon application to the skin.

Another object of the present invention is to provide a water-in-oil emulsified solid cosmetic composition having an excellent usability, i.e., extendability and refreshing feeling, and capable of being filled in a wide variety of containers.

A further object of the present invention is to provide a water-in-oil emulsified solid cosmetic composition having good cosmetic finish durability, in addition to the above-mentioned stability and usability.

Other objects and advantages of the present invention will be apparent from the following description.

In accordance with the present invention, there is provided a water-in-oil type emulsified solid cosmetic composition comprising 5% to 80% by weight of a silicone oil, 3% to 30% by weight of a solid wax, water, 5% to 85% by weight of at least one polyoxyalkylene modified organopolysiloxane having the following structures (1), (2), (3), and/or (4), and 5% by weight or more of water, all based upon the total amount of the composition.

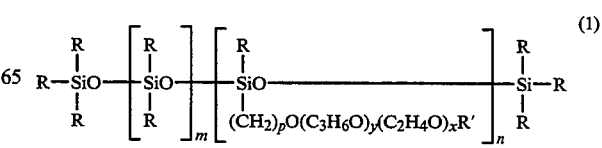

(1)

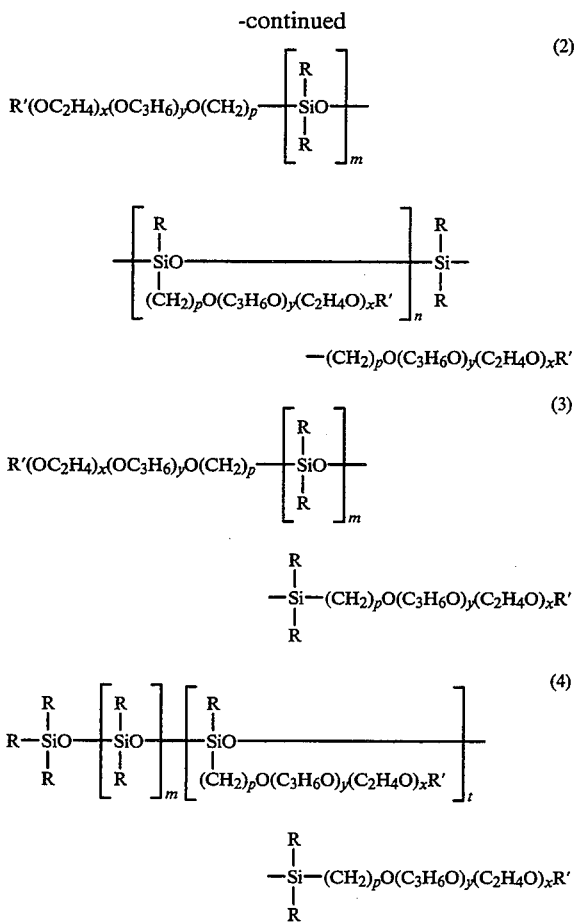

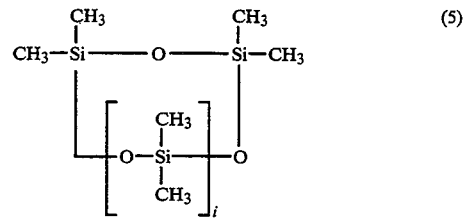

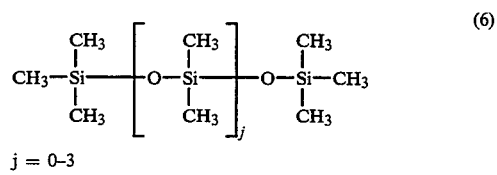

where R is an alkyl group having 1 to 3 carbon atoms or a phenyl group, R' is hydrogen or an alkyl group having 1 to 12 carbon atoms, p is an integer of 1 to 5, m is an integer of 5 to 100, n and x are integers of 1 to 50, and t and y are integers of 0 to 50.

Polyoxyalkylene modified organopolysiloxane preferably contains 5 to 40% by weight of polyoxyalkylene groups in the molecule and the polyoxyalkylene modified organopolysiloxane preferably has a molecular weight of 1000 or more.

In accordance with the present invention, there is also provided a water-in-oil type emulsified solid cosmetic comprising 5% to 85% by weight of an oil component including 30% to 100% by weight, based on the amount of the oil component, of a silicone oil 5% to 20% by weight of an oil-gelling agent, 0.2% to 10% by weight of at least one polyoxyalkylene modified organopolysiloxane selected from the group consisting of those having the above-mentioned structures (1), (2), (3), and (4), and 5% by weight or more of water, all based on the total amount of the composition;

In accordance with the present invention, there is further provided a water-in-oil type emulsified solid cosmetic composition comprising 5% to 85% by weight of an oil, 5% to 20% by weight of at least one component selected from the group consisting of solid waxes and oil-gelling agents, 5% by weight or more of water, 0.2% to 10% by weight of a lipophilic surfactant, and 5% to 50% by weight of a hydrophobically treated powder, all based upon the total amount of the composition.

DESCRIPTION OF THE PREFERRED EMBODIMENT

The term "water-in-oil type emulsified solid cosmetic composition" used herein means compositions (including a paste) which are solidified, without providing a fluidizability, at a temperature range (i.e., 0° C.–50° C.), at which cosmetics are generally used.

The silicone oils usable in the first embodiment of the present invention include those conventionally used in cosmetics compositions. Examples of such oils are dialkyl polysiloxanes such as dimethyl polysiloxane, dimethyl cyclopolysiloxane, and diethyl polysiloxane; alkylaryl polysiloxanes such as methylphenyl polysiloxane; diaryl polysiloxane; fatty acid modified polysiloxanes; higher alcohol modified polysiloxanes; amino modified polysiloxane; and polyoxyalkylene modified organopolysiloxanes. These silicon oils may be used alone or in any mixture thereof.

The amount of the silicone oil formulated into the composition depends upon the other oil components, but the silicon oil is preferably used in an amount of about 30% to 97% by weight of the oil phase or about 5% to 85% by weight of the total cosmetic composition. Especially, volatile silicone oil having the following structure (5) or (6) can be preferably used to advantageously provide a refreshing feeling upon application. The preferable formulated amount is 30% to 97% by weight of the oil phase or 5% to 85% by weight of the total composition.

The solid waxes usable in the first embodiment of the present invention include those conventionally used in cosmetic compositions. Examples of such waxes are petroleum waxes such as paraffin wax, microcrystalline wax, and the like; mineral waxes such as ozokerite, ceresin, and the like; and natural waxes such as carnauba wax, candelilla wax, and the like; and mixed waxes, having a melting point of 50° C. or more. Especially, the use of waxes containing linear and/or branched hydrocarbon with 25 to 52 carbon atoms, as a main constituent is preferable.

Although the types of wax used are selected in accordance with the types of oil used, wax esters such as carnauba wax and candelilla wax are preferably used in combination with the linear and/or branched hydrocarbon wax. Furthermore, the hydrocarbon solid waxes generally available on the market are obtained in the form of a mixture and therefore, these waxes have a different number of carbon atoms, and include isoparaffin and naphthene. Even where the wax contains hydrocarbons having 25 to 52 carbon atoms as a main component, those waxes may be used in the present invention.

Although the amount of solid wax to be formulated may be adjusted based upon the desired hardness, the preferable ratio (by weight) of the oil component to the solid wax is 20:1 to 3:1, and the preferable amount of the solid wax is 5% to 20% by weight.

The polyoxyalkylene modified organopolysiloxanes usable in the present invention are those having the above-mentioned formulae (1), (2), (3), and (4). The polyoxalkylene modified organopolysiloxane preferably contains 5% to 40% by weight of polyoxyalkylene groups in the molecule, and the molecular weight of the polyoxyalkylene modified organopolysiloxane is preferably 1000 or more, specially 2000 to 20000.

Although the amount of the polyoxyalkylene modified organopolysiloxane formulated depends upon the amount of the aqueous phase to be emulsified, the preferable amount formulated is 0.2% to 10% by weight.

The amount of the water formulated in the present invention is 5% by weight or more, especially 10% to 60% by weight, of the total cosmetic composition. When too small, an amount of the water is formulated, the desired cool and refreshing feeling upon application is not obtained. To obtain a very good refreshing feeling upon application, preferably the water is formulated into the cosmetic compositions in an amount of 10% by weight or more of the total cosmetic composition.

In the second embodiment of the present invention, the silicone oils set forth in the above-mentioned first embodiment of the present invention are usable in an amount of 30% to 100% by weight of the total oil component and 5% to 80% by weight of the total cosmetic composition. The volatile silicone oil having the above-mentioned structure (5) or (6) can be preferably used to advantageously provide a refreshing feeling upon application in an amount of, preferably, 10% to 60% by weight of the total amount of the cosmetic composition.

According to the second embodiment of the present invention, in addition to the above-mentioned silicone oil, other oils can be formulated into the present water-in-oil type solid cosmetic composition. Examples of such oils are avocado oil, camellia oil, turtle oil, macadamia nut oil, corn oil, mink oil, olive oil, rapeseed oil, egg yalk oil, sesame oil, persic oil, wheat germ oil, pasanqua oil, castor oil, linseed oil, safflower oil, cottonseed oil, perillic oil, soybean oil, peanut oil, tea seed oil, kaya oil (or miscanthus oil), rice bran oil, china paulownia oil, Japanese paulownia oil, jojoba oil, rice germ oil, glycerol trioctanate, glycerol triisopalmitate, trimethylolpropane triisostearate, isopropyl myristate, glycerol tri-2-ethylhexanoate, pentaerythritol tetra-2-ethylhexanoate, lanolin, liquid lanolin, liquid paraffin, squalane, pristane, isoparaffin, squalane, vaseline, and the like. In addition to the above-exemplified oils, the above-mentioned various waxes or other commercially available waxes also can be used as the oil component in the second embodiment of the present invention.

The oil-gelling agents usable in the second embodiment of the present invention include, for example, condensates of p-benzaldehyde and penta or more hydric alcohols such as dibenzylidene sorbitol, tribenzylidene sorbitol, dibenzylidene xylitol, and p-methoxybenzylidene sorbitol; metallic soap such as calcium stearate, calcium palmitate, lithium 2-ethylhexanate, and aluminum 12-hydroxystearate; the derivatives (e.g., amides, esters, and amines) of N-acylamino acid such as lauroylglutamic dibutyl amide, lauroylglutamic stearyl amide, dicaproyl lysine lauryl amine salt, dicaproyl lysine lauryl ester, and dicaproyl lysine lauroylphenylalanine laurylamide; dextrin fatty acid ester comprising acid hydrolyzates of starch saturated fatty acid esters having an ester substitution degree of 30% or more; and 12-hydroxystearic acid. These oil-gelling agents can be used alone or in any mixture thereof in the present cosmetic composition. The amount of the oil-gelling agent formulated into the cosmetic composition can be adjusted depending upon the desired hardness of the cosmetic composition, and is preferably, as a ratio of the oil component to the oil-gelling agent, 20:1 to 3:1 and 5% to 20% by weight of the total amount of the cosmetic composition.

The polyoxyalkylene modified organopolysiloxane usable in the second embodiment of the present invention is mentioned above, in the same formulation amount.

According to the second embodiment of the present invention, 5% to 50% by weight of a powder, which is conventionally used in cosmetic compositions, can be optionally formulated into the water-in-oil type emulsified solid cosmetic composition. Examples of such powders are, as an inorganic powder, clay mineral powders, such as talc, mica, sericite, silica, magnesium silicate, calcium silicate, aluminum silicate, bentonite and montmorilonite; and pearl pigments such as alumina, barium sulfate, calcium secondary phosphate, calcium carbonate, titanium oxide, finely divided titanium oxide having a particle size of 0.1 $\mu$m, zirconium oxide, zinc oxide, hydroxy apatite, iron oxide, iron titanate, ultramarine blue, Prussian blue, chromium oxide, chromium hydroxide, cobalt oxide, cobalt titanate, and titanium oxide coated mica. Examples of the organic powders are polyesters, polyethylenes, polystyrenes, methyl methacrylate resins, celluloses, 12-nylons, 6-nylons, styrene-acrylic acid copolymers, polypropylenes, vinyl chloride polymers, tetrafluoroethylene polymers, boron nitride, fish scale guanine, raked tar color dyes (e.g., Red #3, Red #4, Red #203), raked natural color dyes; composite powders of inorganic powder and organic powder also may be used as the powder component.

In the present invention, the above-mentioned powders treated with a hydrophobical treatment agent are especially preferably used. The hydrophobical treatment advantageously results in a stability against color separation and in an improvement of the cosmetic finish durability (e.g., water resistance, sebum resistance, and perspiration resistance. Especially when various kinds of powders are formulated into the cosmetic products, it is important to control the dispersibility of each powder. The dispersibility can be uniformized by the hydrophobical treatment of each powder and, therefore, color separation and the like rarely occur and the stability is increased. Furthermore, since the hydrophobically treated powder is resistant to moisture, the cosmetic finish durability is also improved.

Examples of the hydrophobical treatment agents are dextrin fatty acid esters, metallic soaps, silicon compounds, dibenzilidene sorbitol, and similar organic compounds. The hydrophobical treatment methods using these treatment agents are disclosed in, for examples, Japanese Unexamined Patent Publication (Kokai) Nos. 62-205165, 56-16404, 59-76009, 60-163973, 63-113081, and 63-113082 and Japanese Examined Patent Publication (Kokoku) Nos. 45-15394, 61-58499, and 56-43264.

The above-mentioned powders may be used alone or in any mixture thereof, in an amount of 5% to 50% by weight of the total amount of the cosmetic composition, especially, 15% to 40% by weight in the case of foundation compositions. When the amount of the total powders is less than 5% by weight, the desired make-up effects can not be obtained because of too thin a coating. Contrary to this, when the amount of the total powders is more than 50% by weight, the desired easy or light stretchability of the resultant cosmetic composition can not be obtained.

In the third embodiment of the present invention, the water-in-oil type emulsified solid cosmetic composition comprising an oil component, a solid wax and/or an oil-gelling agent, water, a liophilic surfactant, and a hydrophobically treated powder is provided. As the oil component, the solid wax, the oil-gelling agent, and the hydrophobically treated powder, those set forth in the above-mentioned first and/or second embodiments of the present invention in the same amounts as mentioned above.

The hydrophobically treated surfactants usable in the third embodiment of the present invention include those having an HLB value of 8 or less, as determined by a Kawakami method. Examples of such surfactants are preferably sorbitan monoisostearate, sorbitan disostearate, sorbitan sesquiisostearate, sorbitan monooleate, sorbitan dioleate, sorbitan sequioleate, glyceryl monoisostearate, glyceryl diisostearate, glyceryl sesquiisostearate, glyceryl monooleate, glyceryl dioleate, glyceryl sesquioleate, diglyceryl diisostearate, diglyceryl dioleate, diglycerine monoisostearyl ether, diglycerine diisostearyl ether. These surfactants may be formulated, alone or in any mixture thereof, into the cosmetic composition in an amount of 0.2% to 10% by weight of the total amount of the cosmetic composition.

According to the present invention, in addition to the above-mentioned essential constituents, a pigment powder may be formulated.

The pigments usable in the present invention may include those conventionally used in the cosmetic composition, such as inorganic pigments, organic pigments, and metallic pigments. Examples of such inorganic pigments are talc, kaolin, calcium carbonite, zinc oxide, titanium dioxide, red iron oxide, yellow iron oxide, black iron oxide, ultramarine blue, titanium coated mica, bismuth oxychloride, red oxide (rouge), binding pigments, ultramarine pink, chromium hydroxide, mica titanium, chromium oxide, cobalt aluminum oxide, prussian blue, carbon black, silicic anhydride, magnesium silicate, bentonite, mica, zirconium oxide, magnesium oxide, zinc oxide, titanium oxide, light calcium carbonate, heavy magnesium carbonate, and calamine. The use of a hydrophobically treated pigment powder is especially preferable. For the hydrophobical treatment, any conventional method may be used as long as the surface is hydrophobically treated. Examples of such methods are treatment of the surface with silicone having a high viscosity; coating of the surface with silicone resin reacted with alkyl hydrogen polysiloxane or those further treated with alkene; treatment with cationic, anionic, and/or nonionic surfanctants; and coating of the surface with wax. Although there are no critical limitations to the amount of the pigment, the amount of the pigment powder formulated is preferably 50% by weight or less of the total amount of the cosmetic composition.

In the emulsified composition according to the present invention, any components conventionally used can be formulated within the range which does not impair the effect of the present invention. Examples of such components are as follows.

As the aqueous phase component, alcohols such as ethanol, humectants including polyols; mucopolysaccharides such as sodium hyaluronate and sodium chondroitin sulfate; and organic acids and organic acid salts such as amino acids and their salts, and hydroxyacids, (e.g., citric acid, malic acid, lactic acid and their salts, can be exemplified.

As the oil phase components, solid or semi-solid oil components such as petrolatum, lanolin, ceresine, silicone wax, higher fatty acids, higher alcohols; fluid oil components such as squalane, liquid paraffin, ester oils, and triglycerides; surfactants such as cationic surfactants, anionic surfactants, nonionic surfactants: drugs such as vitamin E and vitamin E acetate; styptics; antioxidants; preservatives; flavors; pH controllers such as sodium biphosphate; thickeners; and UV-ray absorbers can be formulated, of these components, the humectants such as polyols, mucopolysaccharides (e.g., sodium hyaluronate), organic acids, organic acid salts (e.g., amino acids, amino acid salts hydroxyacid salts) are preferably formulated to suppress the water volatilization to within the range which does not impair the effect of the present invention.

According to the present invention, by using the oil phase containing the silicone oil and solid wax, as another phase, and the polyoxyalkylene modified organopolysiloxane, as an emulsifier, a large amount of water can be formulated and the non-fluidizable solid water-in-oil type emulsified cosmetic composition having an excellent stability (i.e., water volatilization is small and "cracks" are not generated) and providing novel application feelings (i.e., cool feeling upon application) and having an excellent usability (i.e., excellent extendability and refreshing feeling) can be obtained. Especially, when the present water-in-oil type emulsified solid cosmetic composition is used as a make-up cosmetic composition, an advantageous make-up cosmetic composition capable of providing a prolonged retainability of the cosmetic finish and a good feeling upon application, and having various humectants and drugs in the aqueous component or even in the solid cosmetic composition, can be obtained. Furthermore, due to the excellent stability thereof, the present cosmetic composition may be filled in a wide variety of containers having various shapes. Especially in the case of the third embodiment of the present invention, a good cosmetic finish durability also can be obtained.

EXAMPLES

The present invention will now be further illustrated in detail by, but is by no means limited to, the following Examples, wherein "percentages" are all by weight unless otherwise noted.

Example 1

| Ingredient | % |
|---|---|
| (1) Decamethylcyclopentasiloxane | 38 |
| (2) Aristo wax (165° F.) (solid wax) | 10 |
| (3) Polyoxyalkylene modified organo-polysiloxane[*1] | 2 |
| (4) Deionized water | 50 |

[*1] In the formula (1), average molecular weight = 6000, R = methyl, R' = hydrogen, p = 3, y = o, x = 20

The components (1)–(3) were heated at 80° C., followed by adding the component (4) thereto. After emulsifying, the mixture was cooled at room temperature to obtain the desired water-in-oil type emulsified solid cosmetic composition.

Similarly, according to the same procedure as in Example 1, the following cosmetic compositions of Examples 2 to 4 and Comparative Examples 1 to 6 were prepared.

Example 2

| Ingredient | % |
| --- | --- |
| (1) Decamethylcyclopentasiloxane | 38 |
| (2) Ceresin B | 10 |
| (3) Polyoxyalkylene modified organopolysiloxane*1 | 2 |
| (4) Deionized water | 50 |

Example 3

| Ingredient | % |
| --- | --- |
| (1) Decamethylcyclopentasiloxane | 38 |
| (2) PM wax 82 (solid wax) | 10 |
| (3) Polyoxyalkylene modified organopolysiloxane*1 | 2 |
| (4) Deionized water | 50 |

Comparative Example 1

| Ingredient | % |
| --- | --- |
| (1) Decamethylcyclopentasiloxane | 38 |
| (2) Partial ester of dextrin palmitate | 10 |
| (3) Polyoxyalkylene modified organopolysiloxane*1 | 2 |
| (4) Deionized water | 50 |

Comparative Example 2

| Ingredient | % |
| --- | --- |
| (1) Decamethylcyclopentasiloxane | 38 |
| (2) Stearic acid | 10 |
| (3) Polyoxyalkylene modified organopolysiloxane*1 | 2 |
| (4) Deionized water | 50 |

Comparative Example 3

| Ingredient | % |
| --- | --- |
| (1) Decamethylcyclopentasiloxane | 38 |
| (2) Hydrogenated caster oil | 10 |
| (3) Polyoxyalkylene modified organopolysiloxane*1 | 2 |
| (4) Deionized water | 50 |

The water-in-oil type emulsified solid cosmetic compositions obtained in Examples 1–3 and Comparative Examples 1–3 using various waxes were filled in glass bottles and the glass bottles were allowed to stand, without caps, in constant temperature baths at 25° C. and 50° C. The weight loss with the elapse of time and the stability (e.g., generation of cracks and separation) were determined. The results are shown in Table 1.

TABLE 1

| | Standing temperature without cap | Weight loss (%) with elapse of time*1 | | | Stability*2 |
| --- | --- | --- | --- | --- | --- |
| | | 1 week | 2 week | 3 week | |
| Example 1 | 25° C. | 0.4 | 1.1 | 1.4 | Good |
| | 50° C. | 2.3 | 3.7 | 4.9 | |
| Example 2 | 25° C. | 0.6 | 1.0 | 1.4 | Good |
| | 50° C. | 2.2 | 4.6 | 7.6 | |
| Example 3 | 25° C. | 1.0 | 1.8 | 2.4 | Good |
| | 50° C. | 5.3 | 12.8 | 17.8 | |
| Comparative Example 1 | 25° C. | 23.0 | 49.7 | 96.8 | Poor |
| | 50° C. | 98.6 | 98.9 | 99.0 | |
| Comparative Example 2 | 25° C. | 20.7 | 44.3 | 92.2 | Poor |
| | 50° C. | 59.3 | 75.5 | 97.2 | |
| Comparative Example 3 | 25° C. | 24.1 | 48.3 | 95.4 | Poor |
| | 50° C. | 64.3 | 88.8 | 98.1 | |

*1Weight loss with elapse of time =

$$\frac{\text{(Initial weight} - \text{Weight with elapse of time)}}{\text{Weight of volatile component}} \times 100$$

*2Stability:
Good ... No separation and no cracks at 25° C. or 50° C. after standing for 3 weeks
Poor ... Separation and/or cracks observed at 25° C. or 50° C. after standing for 3 weeks As clear from the results shown in Table 1, the cosmetic compositions of Examples 1 to 3 are stable and show no weight loss.

Example 4

| Ingredient | % |
| --- | --- |
| (1) Dimethylpolysiloxane (6 cs) | 38 |
| (2) Aristo wax (165° F.) | 10 |
| (3) Polyoxyalkylene modified organopolysiloxane*1 | 2 |
| (4) Deionized water | 50 |

Comparative Example 4

| Ingredient | % |
| --- | --- |
| (1) Decamethylcyclopentasiloxane | 38 |
| (2) Aristo wax (165° F.) | 10 |
| (3) Diglyceryl diisostearate | 2 |
| (4) Deionized water | 50 |

Comparative Example 5

| Ingredient | % |
| --- | --- |
| (1) Liquid paraffin | 38 |
| (2) Aristo wax (165° F.) | 10 |
| (3) Polyoxyalkylene modified organopolysiloxane | 2 |
| (4) Deionized water | 50 |

Comparative Example 6

| Ingredient | % |
| --- | --- |
| (1) Decamethylcyclopentasiloxane | 85 |
| (2) Aristo wax (165° F.) | 10 |
| (3) Polyoxyalkylene modified organopolysiloxane*2 | 2 |
| (4) Deionized water | 3 |

*2In the formula (2), average molecular weight = 3000, R = methyl, R' = hydrogen, p = 3, y = o, x = 11

The feeling upon application of the water-in-oil type emulsified solid cosmetic compositions of Examples 1 and 4 and Comparative Examples 5 and 6 was evaluated. Note, separation occurred in the cosmetic composition of Comparative Example 4 immediately after preparation and a good solid state was not obtained.

The results are shown in Table 2.

TABLE 2

|  | Cooling feeling | Refreshing feeling | Extendability |
|---|---|---|---|
| Example 1 | ○ | ○ | ○ |
| Example 4 | ○ | ○ | ○ |
| Comparative Example 5 | Δ | x | Δ |
| Comparative Example 6 | x | ○ | ○ |

Panel: 20 members
○ ... Yes ... 15 members or more
Δ ... Yes ... 7–14 members
x ... Yes ... 6 members or less Example 5: Foundation

| Ingredient | % |
|---|---|
| (1) Decamethylcyclopentasiloxane | 38 |
| (2) Aristo wax (165° F.) | 10 |
| (3) Polyoxyalkylene modified organopolysiloxane*3 | 2 |
| (4) Hydrophobically treated pigment powder | 30 |
| (5) Deionized water | 20 |
| (6) Preservative | q.s. |
| (7) Flavor | q.s. |

*3 In the formula (3), average molecular weight = 9000, R = methyl, R' = hydrogen, p = 3, y = o, x = 20

The components 1 to 3 and 7 were heated to dissolve at 80° C., followed by adding the component 4, and the mixture was dispersed at 80° C. in a homogenizer. Thereafter, a mixture of the components 5 and 6 previously heated to 80° C. was added to this mixture to effect an emulsification. The resultant emulsified composition was then filled in a container and allowed to cool to room temperature, and thus the desired water-in-oil type emulsified solid foundation was obtained.

Comparative Example 7

| Ingredient | % |
|---|---|
| (1) Decamethylcyclopentasiloxane | 38 |
| (2) Carnauba wax | 10 |
| (3) Polyoxyalkylene modified organopolysiloxane*3 | 2 |
| (4) Hydrophobically treated pigment powder | 30 |
| (5) Deionized water | 20 |
| (6) Preservative | q.s. |
| (7) Flavor | q.s. |

The composition was prepared in the same manner as in Example 5.

The resultant cosmetic foundations of the Example 5 and Comparative Example 7 were evaluated in the same manner as in Example 1.

The results are shown in Table 3. As clear from the results shown in Table 3, the solid foundation of Example 5 was stable and the weight loss by volatilization was small.

TABLE 3

| | Standing temperature without cap | Weight loss (%) with elapse of time* | | | Stability* |
|---|---|---|---|---|---|
| | | 1 week | 2 week | 3 week | |
| Example 5 | 25° C. | 2.0 | 3.8 | 5.1 | Good |
| | 50° C. | 7.8 | 14.4 | 19.9 | |
| Comparative Example 7 | 25° C. | 7.1 | 12.6 | 21.0 | Poor |
| | 50° C. | 60.7 | 92.2 | 98.0 | |

*see Table 1

Example 6

Stick Type Emulsified Foundation

| Ingredient | % |
|---|---|
| (1) Octamethylcyclotetrasiloxane | 15 |
| (2) Decamethylcyclopentasiloxane | 20 |
| (3) Glyceryl triisooctanate | 3 |
| (4) Polyoxyalkylene modified organopolysiloxane*4 | 2 |
| (5) Ceresin wax | 10 |
| (6) Hydrophobically treated pigment powder | 30 |
| (7) Flavor | q.s. |
| (8) Deionized water | 17 |
| (9) Glycerol | 2 |
| (10) 1,3-Butylene glycol | 1 |
| (11) Preservative | q.s. |

*4 In the formula (3), average molecular weight = 9000, R = methyl, R' = hydrogen, p = 3, y = 2, x = 30

The components (1)–(5) and (7) were heated to 80° C. and, after dissolution, the component (6) was added thereto, followed by dispersing at 80° C. in a homogenizer. Further, a mixture of the components (8)–(11) previously heated to 80° C. was added to emulsify the mixture, and thereafter, the mixture was filled into a stick type container, followed by cooling to a room temperature, and thus the desired stick type emulsified foundation was obtained.

Example 7

Urea Formulated Solid Cosmetics

| Ingredient | % |
|---|---|
| (1) Trimethylsiloxy silicate | 3 |
| (2) Dimethylpolysiloxane | 10 |
| (3) Decamethylcyclopentasiloxane | 20 |
| (4) Hydrocarbon wax (C32–C40) | 10 |
| (5) Polyoxyalkylene modified organopolysiloxane*1 | 2 |
| (6) Deionized water | 46 |
| (7) Urea | 3 |
| (8) Glycine | 3 |
| (9) Diglycerol | 2 |
| (10) Propylene glycol | 1 |
| (11) Preservative | q.s. |

The components (1)–(5) were heated to 80° C. and, after dissolution, a mixture of the components (6)–(11) previously heated to 80° C. was added thereto, followed by emulsifying and dispersing, and thereafter, the mixture was filled into an ointment container, followed by cooling to room temperature, and thus a desired solid cosmetic composition containing urea was obtained.

Example 8

Compact Type Emulsified Foundation

| Ingredient | % |
|---|---|
| (1) Decamethylcyclopentasiloxane | 36 |
| (2) Dimethylpolysiloxane (6 c.s.) | 2 |
| (3) Jojoba oil | 4 |
| (4) Ceresin | 8 |
| (5) Microcrystalline wax | 1 |
| (6) Polyoxyalkylene modified organopolysiloxane*3 | 2 |
| (7) Hydrophobically treated pigment powder | 20 |
| (8) Deionized water | 10 |
| (9) Glycerol | 15 |
| (10) 1,3-Butyrene glycol | 2 |
| (11) Preservative | q.s. |
| (12) Perfume | q.s. |

The components (1)–(6) and (12) were heated to 70° C., and then the component (7) was added thereto, followed by dispersing. Then, a mixture of the components (8)–(11) previously heated to 80° C. was added thereto followed by emulsifying and dispersing, and thereafter, the resultant dispersion in the fluidizable state was filled in an inner dish, followed by cooling to room temperature, and then placed in a compact type container to obtain the desired compact type emulsified foundation. The resultant emulsified foundation has a moisturizing, cool and refreshing feeling and is easy to carry as a portable cosmetic.

The following cosmetic compositions were prepared as follows. Namely, the oil phase components were dissolved upon heating at 80° C., followed by dispersing the powder. Then, the aqueous components previously heated to 80° C. were emulsified and dispersed therein, followed by filling in a fluidizable state into a container, and thereafter, the container was cooled to obtain the desired product. All of the products had a good stability and an excellent applicability and usability, such as a refreshing feeling.

Example 9

Rouge

| Ingredients | % |
| --- | --- |
| (1) Dimethylpolysiloxane (1.5 c.s.) | 20 |
| (2) Decamethylcyclopentasiloxane | 10 |
| (3) Cetyl isooctanate | 15 |
| (4) Polyoxyalkylene modified organopolysiloxane*5 | 3 |
| (5) Hydrocarbon wax | 12 |
| (6) Flavor | q.s. |
| (7) Hydrophobically treated pigment powder | 30 |
| (8) Deionized water | 6.9 |
| (9) Sodium hyaluronate | 0.1 |
| (10) Sodium chondroitin sulfate | 1.5 |
| (11) Polyethylene glycol | 1.5 |
| (12) Preservative | q.s. |

Example 10

Lipstick

| Ingredient | % |
| --- | --- |
| (1) Octamethylcyclotetrasiloxane | 10 |
| (2) Dimethylpolysiloxane (6 cs) | 20 |
| (3) Carnauba wax | 2.8 |
| (4) Aristo wax (165° F.) | 8 |
| (5) Polyoxyalkylene modified organopolysiloxane*1 | 5 |
| (6) Red iron oxide | 0.3 |
| (7) Yellow iron oxide | 1 |
| (8) Red #204 | 0.7 |
| (9) Dibutylhydroxy toluene | q.s. |
| (10) Flavor | q.s. |
| (11) Deionized water | 51.4 |
| (12) Atelocolagen | 0.3 |
| (13) Sodium pyrrolidone carboxylate | 0.5 |

Example 11

| Ingredient | % |
| --- | --- |
| (1) Squalane | 10 |
| (2) Lanolin | 2 |
| (3) Octamethylcyclotetrasiloxane | 27.69 |
| (4) Isoparaffin (b.p. = 155° C.) | 10 |
| (5) Trimethylsiloxy silicate | 3 |
| (6) Hydrocarbon wax | 8 |
| (7) Polyoxyalkylene modified organopolysiloxane*3 | 3 |
| (8) Deionized water | 30 |

| Ingredient | % |
| --- | --- |
| (9) Glycerol | 5 |
| (10) Sodium lactate | 0.3 |
| (11) Sodium l-glutamate | 0.3 |
| (12) Sodium hyaluronate | 0.1 |
| (13) Sorbitol | 0.5 |
| (14) Red #202 | 0.01 |
| (15) Menthol | 0.1 |
| (16) Flavor | q.s. |

Example 12

| Ingredient | % |
| --- | --- |
| (1) Decamethylcyclopentasiloxane | 20 |
| (2) Cetyl isooctanate | 18 |
| (3) 12-Hydroxystearic acid | 10 |
| (4) Polyoxyalkylene modified organopolysiloxane*5 | 2 |
| (5) Deionized water | 50 |

*5In the formula (1), average molecular weight = 6000, R = methyl, R' = hydrogen, p = 3, y = 0, x = 28

Preparation

The components (1)–(4) were heated at 80° C., followed by adding thereto the component (5). After emulsifying, the mixture was cooled to a room temperature to obtain the desired water-in-oil type emulsified solid cosmetic composition.

Similarly, according to the same procedure as in Example 12, the following cosmetic compositions of Examples 13 and 14 and Comparative Examples 8 to 11 were prepared.

Example 13

| Ingredient | % |
| --- | --- |
| (1) Decamethylcyclopentasiloxane | 20 |
| (2) Cetyl isooctanate | 18 |
| (3) Dextrin palmitate | 10 |
| (4) Polyoxyalkylene modified organopolysiloxane*5 | 2 |
| (5) Deionized water | 50 |

Comparative Example 8

| Ingredient | % |
| --- | --- |
| (1) Decamethylcyclopentasiloxane | 20 |
| (2) Cetyl isooctanate | 18 |
| (3) Carnauba wax | 10 |
| (4) Polyoxyalkylene modified organopolysiloxane*5 | 2 |
| (5) Deionized water | 50 |

Comparative Example 9

| Ingredient | % |
| --- | --- |
| (1) Decamethylcyclopentasiloxane | 20 |
| (2) Cetyl isooctanate | 18 |
| (3) Stearic acid | 10 |
| (4) Polyoxyethylene (6 mole) sorbitan monooleate | 2 |
| (5) Deionized water | 50 |

The water-in-oil type emulsified solid cosmetic compositions obtained in Examples 1 and 2 and Comparative Examples 1 and 2 were filled in glass bottles and were allowed to stand, without caps, in constant temperature baths at 25° C. and 50° C. The stability, such as generation of cracks and separation, was evaluated in the same manner as in Examples 1 to 3.

The results are shown in Table 4.

TABLE 4

| No. | Temperature | stability |
|---|---|---|
| Example 12 | 25° | Good |
|  | 50° | " |
| Example 13 | 25° | " |
|  | 50° | " |
| Comparative Example 8 | 25° | Poor |
|  | 50° | " |
| Comparative Example 9 | 25° | " |
|  | 50° | " |

As is clear from the results shown in Table 4, the water-in-oil type emulsified solid cosmetic compositions of Examples 12 and 13 exhibited a good stability.

Example 14

| Ingredient | % |
|---|---|
| (1) Methylphenylpolysiloxane | 20 |
| (2) Cetyl isooctanate | 18 |
| (3) Dextrin palmitate | 10 |
| (4) Polyoxyalkylene modified organopolysiloxane*5 | 2 |
| (5) Deionized water | 50 |

Comparative Example 10

| Ingredient | % |
|---|---|
| (1) Liquid paraffin | 20 |
| (2) Cetyl isooctanate | 18 |
| (3) Dextrin palmitate | 10 |
| (4) Polyoxyalkylene modified organopolysiloxane*5 | 2 |
| (5) Deionized water | 50 |

Comparative Example 11

| Ingredient | % |
|---|---|
| (1) Decamethylcyclopentasiloxane | 67 |
| (2) Cetyl isooctanate | 18 |
| (3) Dextrin palmitate | 10 |
| (4) Polyoxyalkylene modified organopolysiloxane*5 | 2 |
| (5) Deionized water | 3 |

The feeling upon application of the resultant water-in-oil type emulsified solid cosmetic compositions of Examples 12 and 14 and Comparative Examples 10 and 11 was evaluated from the organoleptical test using a panel of 20 members. The results are evaluated as follows.

o ... Positive response by 15 members or more
Δ ... Positive response by 7 to 14 members
x ... Positive response by 6 members or less The results are shown in Table 5.

TABLE 5

| No. | Cooling feeling | Refreshing feeling | Extendability |
|---|---|---|---|
| Example 12 | o | o | o |
| Example 14 | o | o | o |
| Comparative Example 10 | Δ | x | Δ |
| Comparative Example 11 | x | o | o |

Example 15

| Ingredient | % |
|---|---|
| (1) Decamethylcyclopentasiloxane | 10 |
| (2) Methylphenylpolysiloxane | 10 |
| (3) Cetyl isooctanate | 18 |
| (4) Dextrin palmitate | 10 |
| (5) Polyoxyalkylene modified organopolysiloxane*6 | 2 |
| (6) Silicone treated powder | 30 |
| (7) Deionized water | balance |
| (8) Preservative | q.s. |
| (9) Flavor | q.s. |

*6 Average molecular weight = 12,000, R = methyl, R' = hydrogen, p = 3, y = 0 and x = 32 in the formula (2).

The components (1) to (5) and (9) were dissolved by heating to 80° C., followed by adding the component (6), and the mixture was heated to 80° C. and dispersed in a homogenizer. Thereafter, a mixture of the components (7) and (8) previously heated to 80° C. was added to the resultant mixture to effect the emulsification. The resultant emulsified composition was filled in a container and allowed to cool to room temperature. Thus, the desired water-in-oil type emulsified solid foundation was obtained.

The silicone treated powder used above was obtained, according to a method disclosed in Japanese Unexamined Publication (Kokai) Nos. 63-113081 and 63-113082, by reacting a mixture of 3.65 parts of mica, 5.0 parts of titanium dioxide, 0.25 parts of iron oxide (red), 1.0 part of iron oxide (yellow), and 0.1 part of iron oxide (black) with tetramethyltetrahydrogen cyclosiloxane, followed by the addition reaction thereto of tetradecene. The silicone treated powder used hereinbelow was obtained in the same manner.

Example 16

Emulsified Foundation

| Ingredient | % |
|---|---|
| (1) Octamethylcyclotetrasiloxane | 15 |
| (2) Methylphenyl polysiloxane | 15 |
| (3) Glyceryl triisooctanate | 8 |
| (4) Polyoxyalkylene modified organopolysiloxane*7 | 2 |
| (5) 12-Hydroxystearic acid | 5 |
| (6) Lauroyl glutamic dibutylamide | 5 |
| (7) Calcium stearate treated powder | 30 |
| (8) Flavor | q.s. |
| (9) Deionized water | balance |
| (10) Glycerol | 2 |
| (11) 1,3-Butylene glycol | 1 |
| (12) Preservative | q.s. |

*7 Ave. M.W. = 9000, R = methyl, R' = hydrogen, p = 3, y = 0, x = 25 in the general formula (3).

Preparation

The components (1) to (6) and (8) were heated and dissolved at 80° C., followed by adding the component (7) thereto. The mixture was dispersed at 70° C. in a homogenizer. Furthermore, a mixture of the components (9) to (12) previously heated to 80° C. was added thereto, to effect the emulsification. The resultant emulsified composition was then filled in a container and allowed to cool to room temperature. Thus, the desired stick type emulsified foundation was obtained.

The calcium stearate treated powder used was obtained by mixing the starting mixture of the above-mentioned silicone treated powder with 5%, based on the amount of the powder, of calcium stearate, followed by adding ethanol thereto. The mixture was mixed at 70° C., followed by drying and grinding.

Example 17

Solid Cosmetics

| Ingredient | % |
| --- | --- |
| (1) Trimethylsiloxy silicate | 3 |
| (2) Liquid paraffin | 10 |
| (3) Decamethylcyclopentasiloxane | 20 |
| (4) Dextrin palmitate | 10 |
| (5) Polyoxyalkylene modified organopolysiloxane*8 | 2 |
| (6) Deionized water | balance |
| (7) Urea | 3 |
| (8) Glycine | 3 |
| (9) Diglycerol | 2 |
| (10) Propylene glycol | 1 |
| (11) Preservative | q.s. |

*8 Ave. M.W. = 15000, R = methyl, R' = hydrogen, p = 3, y = 0, x = 34 in the general formula (4).

Preparation

The components (1)–(5) were heated and dissolved at 80° C. A mixture of the components (6)–(11) previously heated at 80° C. was added thereto followed by emulsifying and dispersing. Thereafter, the mixture was filled in an ointment container, followed by cooling to room temperature. Thus, the desired solid cosmetic composition was obtained.

Example 18

Compact Type Emulsified Foundation

| Ingredient | % |
| --- | --- |
| (1) Decamethylcyclopentasiloxane | 15 |
| (2) Methylphenyl polysiloxane | 20 |
| (3) Glyceryl triisooctanate | 5 |
| (4) Jojoba oil | 4 |
| (5) Lauroyl glutamic dibutyl amide | 5 |
| (6) 12-Hydroxystearic acid | 5 |
| (7) Microcrystalline wax | 1 |
| (8) Polyoxyalkylene modified organo-polysiloxane*5 | 2 |
| (9) Silicone treated powder | 20 |
| (10) Deionized water | balance |
| (11) Glycerol | 15 |
| (12) 1,3-Butylene glycol | 2 |
| (13) Preservative | q.s. |
| (14) Flavor | q.s. |

Preparation

The components (1)–(8) and (14) were heated at 80° C., followed by adding the component (9). The mixture was then dispersed. Thereafter, a mixture of the components (10) to (13) previously heated at 80° C. was added thereto, following by emulsifying and dispersing. Thereafter, the resultant dispersion in the fluidizable state was filled in an inner dish, followed by cooling to room temperature, and then placed in a compact type container to obtain the desired compact type emulsified foundation. The resultant emulsified cosmetic compositions obtained in Examples 15 to 18 have a moisturizing, cool and refreshing feeling and are easy to carry as a portable cosmetic.

Example 19

Rouge

| Ingredient | % |
| --- | --- |
| (1) Dimethylpolysiloxane (1.5 cs) | 10 |
| (2) Decamethylcyclopentasiloxane | 10 |
| (3) Cetyl isooctanate | 15 |
| (4) Polyoxyalkylene modified organopolysiloxane*5 | 3 |
| (5) Dextrin palmitate | 12 |
| (6) Flavor | q.s. |
| (7) Dextrine palmitate treated powder | 40 |
| (8) Deionized water | balance |
| (9) sodium hyaluronate | 0.1 |
| (10) Sodium chondroitin sulfate | 1.5 |
| (11) Polyethylene glycol | 1.5 |
| (12) Preservative | q.s. |

Preparation

Oily components were heated and dissolved at 80° C., followed by dispersing the powder therein. Thereafter, aqueous phase components previously heated were emulsified and dispersed therein. The resultant dispersion was filled in a container in the fluidizable state. The container was cooled to room temperature to obtain the desired product.

The dextrin palmitate treated powder was prepared, according to the method disclosed in Japanese Unexamined Patent Publication (Kokai) No. 62-205165, by adding the starting powder mixture used in the preparation of the above-mentioned silicone treated powder to a 5% dextrin fatty acid ester in Isoper E (Exxon Chemicals), followed by removing the solvent after stirring and then drying and grinding.

Example 20:

Lip Treatment

| Ingredient | % |
| --- | --- |
| (1) Squalane | 10 |
| (2) Lanolin | 2 |
| (3) Octamethylcyclotetrasiloxane | 40 |
| (4) Isoparaffin (b.p. 155° C.) | 10 |
| (5) Trimethylsiloxysilicate | 3 |
| (6) Aristo wax (165° F.) | 3 |
| (7) Lauroyl glutamic dibutyl amide | 5 |
| (8) Polyoxyalkylene modified organopolysiloxane*6 | 3 |
| (9) Deionized water | balance |
| (10) Glycerol | 5 |
| (11) Sodium lactate | 0.3 |
| (12) Sodium L-glutamate | 0.3 |
| (13) Sodium hyaluronate | 0.1 |
| (14) Sorbitol | 0.5 |
| (15) Red #202 | 0.01 |
| (16) Menthol | 0.1 |
| (17) Flavor | q.s. |

The oily components were heated and dissolved at 80° C. and, aqueous components previously heated were emulsified and dispersed therein. The resultant dispersion was filled in a container in the fluidizable state, followed by cooling to obtain the desired product.

The cosmetic compositions obtained in Examples 19 and 20 had a good stability and good useability (e.g., refreshness).

Example 21

| Ingredient | % |
| --- | --- |
| (1) Decamethylcyclopentasiloxane | 38.0 |
| (2) Aristo wax (165° F.) | 10.0 |
| (3) Sorbitan diisostearate | 2.0 |
| (4) Silicone treated powder (A)*a | 30.0 |
| (5) Deionized water | balance |
| (6) Preservative | q.s |
| (7) Flavor | q.s |

*a see Example 15

Preparation

The components (1) to (3) and (7) were heated and dissolved at 80° C., followed by adding the component (4) thereto. The mixture was dispersed at 80° C. in a homogenizer. Further, a mixture of the components (5) and (6) previously heated to 80° C. was added and emulsified. Thereafter, the resultant emulsified product was filled in a container, followed by cooling to room temperature to obtain the desired oil-in-water type emulsified solid cosmetic composition.

Comparative Example 12

| Ingredient | % |
| --- | --- |
| (1) Decamethylcyclopentasiloxane | 38.0 |
| (2) Carnauba wax | 10.0 |
| (3) Sorbitan diisostearate | 2.0 |
| (4) Untreated powder (B)*b | 30.0 |
| (5) Deionized water | balance |
| (6) Preservative | q.s |
| (7) Flavor | q.s |

*b The starting powder mixture to the treated powder (A) in Example 21.

Preparation

The cosmetic composition was prepared in the same manner as in Example 21.

The water-in-oil type emulsified solid cosmetic compositions obtained in Example 21 and Comparative Example 12 were filled in glass bottles and the glass bottles were allowed to stand, without caps, in constant temperature baths at 25° C. and 50° C. The weight loss with the elapse of time and the stability (e.g., generation of cracks and separation) were determined. The results are shown in Table 6.

The evaluation methods were as follows.

Weight loss with elapse of time =

$$\frac{(\text{Initial weight} - \text{Weight with elapse of time})}{\text{Weight of volatile component}} \times 100 \quad 1)$$

Stability: 2)

Good ... No separation and no cracks at 25° C. or 50° C. after standing for 3 weeks Poor ... Separation and/or cracks observed at 25° C. or 50° C. after standing for 3 weeks Applicability (20 members panel) 3)

o ... Positive response by ... 15 members or more
Δ ... Positive response by ... 7–14 members
x ... Positive response by ... 6 members or less

TABLE 6

| No. | Standing temperature without cap | Weight loss (%) with elapse of time | | | Stability | Applicability | | | |
| --- | --- | --- | --- | --- | --- | --- | --- | --- | --- |
| | | 1 week | 2 week | 3 week | | Cosmetic finish durability | Extendability | Cool feeling | Refreshness |
| Example 21 | 25° C. | 1.3 | 2.2 | 3.3 | Good | o | o | o | o |
| | 50° C. | 6.5 | 12.1 | 16.5 | | | | | |
| Comparative Example 12 | 25° C. | 7.9 | 16.0 | 12.2 | Poor | x | Δ | o | o |
| | 50° C. | 62.5 | 93.4 | 98.8 | | | | | |

As clear from the results shown in Table 6, the cosmetic composition of Example 21 is stable and shows no weight loss due to the evaporation, and exhibits a good applicability.

Example 22

| Ingredient | % |
| --- | --- |
| (1) Dimethylpolysiloxane | 38.0 |
| (2) Aristo wax (165° F.) | 10.0 |
| (3) Silicone treated powder (A) | 10.0 |
| (4) Sorbitan sesquioleate | 2.0 |
| (5) Deionized water | balance |

(Preparation)

The components (1)–(4) were heated at 80° C., followed by adding the component (5) thereto. After emulsifying, the emulsified mixture was cooled to obtain the desired oil-in-water type emulsified solid cosmetic composition.

The following Examples and Comparative Examples were conducted in the same manner as in Example 22.

Example 23

| Ingredient | % |
| --- | --- |
| (1) Decamethylcyclopentasiloxane | 38.0 |
| (2) Aristo wax (165° F.) | 10.0 |
| (3) Calcium stearate treated powder (C)*c | 10.0 |
| (4) Sorbitan sesquioleate | 2.0 |
| (5) Deionized water | balance |

*c see Example 16

Example 24

| Ingredient | % |
| --- | --- |
| (1) Decamethylcyclopentasiloxane | 38.0 |
| (2) Paraffin wax (155° F.) | 10.0 |
| (3) Dextrin fatty acid ester treated powder (D)*d | 10.0 |
| (4) Sorbitan sesquioleate | 2.0 |
| (5) Deionized water | balance |

*d see Example 19

Example 25

| Ingredient | % |
|---|---|
| (1) Decamethylcyclopentasiloxane | 38.0 |
| (2) Partial ester of dextrin palmitate | 5.0 |
| (3) Aristo wax (165° F.) | 5.0 |
| (4) Silicone treated powder (A) | 10.0 |
| (5) Sorbitan sesquioleate | 2.0 |
| (6) Deionized water | balance |

Comparative Example 13

| Ingredient | % |
|---|---|
| (1) Liquid paraffin | 38.0 |
| (2) Arsito wax (165° F.) | 10.0 |
| (3) Untreated powder (B) | 10.0 |
| (4) Sorbitan sesquioleate | 2.0 |
| (5) Deionized water | balance |

Comparative Example 14

| Ingredient | % |
|---|---|
| (1) Decamethylcyclopentasiloxane | 38.0 |
| (2) Hydrogenated castor oil | 10.0 |
| (3) Untreated powder (B) | 10.0 |
| (4) Sorbitan sesquioleate | 2.0 |
| (5) Deionized water | balance |

Comparative Example 15

| Ingredient | % |
|---|---|
| (1) Decamethylcyclopentasiloxane | 75.0 |
| (2) Aristo wax (165° F.) | 10.0 |
| (3) Sorbitan diisostearate | 2.0 |
| (4) Untreated powder (B) | 10.0 |
| (5) Deionized Water | balance |

The stability and applicability of the water-in-oil type emulsified solid cosmetic compositions obtained in Examples 22–25 and Comparative Examples 13–15 were evaluated in the same manner as mentioned above. The results are shown in Table 7.

TABLE 7

| No. | Standing temperature without cap | Stability | Cosmetic finish durability | Extendability | Cool feeling | Refreshness |
|---|---|---|---|---|---|---|
| Example 22 | 25° C. | Good | ○ | ○ | ○ | ○ |
|  | 50° C. | " |  |  |  |  |
| Example 23 | 25° C. | " | ○ | ○ | ○ | ○ |
|  | 50° C. | " |  |  |  |  |
| Example 24 | 25° C. | " | ○ | ○ | ○ | ○ |
|  | 50° C. | " |  |  |  |  |
| Example 25 | 25° C. | " | ○ | ○ | ○ | ○ |
|  | 50° C. | " |  |  |  |  |
| Comparative Example 13 | 25° C. | Fair | x | ○ | ○ | ○ |
|  | 50° C. | " |  |  |  |  |
| Comparative Example 14 | 25° C. | Poor | x | △ | ○ | ○ |
|  | 50° C. | " |  |  |  |  |
| Comparative Example 15 | 25° C. | Fair | △ | ○ | x | △ |
|  | 50° C. | " |  |  |  |  |

As is clear from the results shown in Table 7, the cosmetic compositions of Examples 22 to 25 are stable without causing the generation of cracks and phase separation and have a good feeling upon application. The cosmetic compositions of Examples 22 to 25 also show very little weight loss due to evaporation.

Example 26

Stick Type Emulsified Foundation

| Ingredient | % |
|---|---|
| (1) Methylphenyl polysiloxane | 5.0 |
| (2) Decamethylcyclopentasiloxane | 20.0 |
| (3) Glyceryl triisooctanate | 3.0 |
| (4) Glyceryl diisostearate | 2.0 |
| (5) Ceresin wax | 7.0 |
| (6) Dibenzylidene sorbitol | 3.0 |
| (7) Calcium stearate treated powder (C) | 30.0 |
| (8) Flavor | q.s. |
| (9) Deionized water | balance |
| (10) Glycerol | 2.0 |
| (11) 1,3-Butylene glycol | 1.0 |
| (12) Preservative | q.s. |

The components (1)–(6) and (8) were heated to 80° C. and, after dissolution, the component (7) was added thereto, followed by dispersing at 80° C. in a homogenizer. Further, a mixture of the components (9)–(12) previously heated to 80° C. was added to emulsify the mixture, and thereafter, the mixture was filled into a stick type container, followed by cooling to a room temperature, and thus the desired stick type emulsified foundation was obtained.

Example 27

Solid Cosmetics

| Ingredient | % |
|---|---|
| (1) Trimethylsiloxy silicate | 3.0 |
| (2) Dimethylpolysiloxane | 10.0 |
| (3) Cetyl isooctanate | 10.0 |
| (4) Squalane | 10.0 |
| (5) Microwax 155 | 10.0 |
| (6) Diglyceryl diisostearate | 2.0 |
| (7) Sorbitan sesquiisostearate | 2.0 |
| (8) Calcium stearate treated talc*e | 7.0 |
| (9) Deionized water | balance |
| (10) Urea | 3.0 |
| (11) Glycine | 3.0 |
| (12) Diglycerol | 2.0 |
| (13) Propylene glycol | 1.0 |
| (14) Preservative | q.s. |

*eTalc was treated in the same manner as in the case of the above-mentioned calcium stearate treated powder (C).

The components (1)–(7) were heated to 80° C. and, after dissolution, the component (8) was added. Thereafter, a mixture of the components (9)–(14) previously heated to 80° C. was added thereto, followed by emulsifying and dispersing, and thereafter, the mixture was filled into an ointment container, followed by cooling to room temperature, and thus a desired solid cosmetic composition containing urea was obtained.

Example 28

Compact Type Emulsified Foundation

| Ingredient | % |
| --- | --- |
| (1) Decamethylcyclopentasiloxane | 36.0 |
| (2) Dimethylpolysiloxane (6 c.s.) | 2.0 |
| (3) Jojoba oil | 4.0 |
| (4) Ceresin | 8.0 |
| (5) Microcrystalline wax | 1.0 |
| (6) Sorbitan diisostearate | 2.0 |
| (7) Silocone treated powder (A) | 20.0 |
| (8) Deionized water | balance |
| (9) Glycerol | 15.0 |
| (10) 1,3-Butyrene glycol | 2.0 |
| (11) Preservative | q.s. |
| (12) Flavor | q.s. |

The components (1)–(6) and (12) were heated to 80° C., and then the component (7) was added thereto, followed by dispersing. Then, a mixture of the components (8)–(11) previously heated to 80° C. was added thereto followed by emulsifying and dispersing, and thereafter, the resultant dispersion in the fluidizable state was filled in an inner dish, followed by cooling to room temperature, and then placed in a compact type container to obtain the desired compact type emulsified foundation. The resultant emulsified foundation has a moisturizing cool and refreshing feeling, good cosmetic finish durability, and is easy to carry as a portable cosmetic.

The following cosmetic compositions were prepared as follows. Namely, the oil phase components were dissolved upon heating at 80° C. were emulsified and dispersed therein, followed by filling in a fluidizable state into a container, and thereafter, the container was cooled to obtain the desired product. All of the products had a good stability and an excellent applicability and usability, such as a refreshing feeling.

Example 29

Rouge

| Ingredient | % |
| --- | --- |
| (1) Liquid paraffin | 20.0 |
| (2) Decamethylcyclopentasiloxane | 10.0 |
| (3) Cetyl isooctanate | 15.0 |
| (4) Diglycerine diisostearyl ether | 3.0 |
| (5) Microwax 155 | 10.0 |
| (6) Dextrin palmitate | 2.0 |
| (7) Flavor | q.s. |
| (8) Dextrin fatty acid ester treated powder (D) | 30.0 |
| (9) Deionized water | 6.9 |
| (10) Sodium hyaluronate | 0.1 |
| (11) Sodium chondroitin sulfate | 1.5 |
| (12) Polyethylene glycol | 1.5 |
| (13) Preservative | q.s. |

Example 30

Lipstick

| Ingredient | % |
| --- | --- |
| (1) Octamethylcyclotetrasiloxane | 10.0 |
| (2) Dimethylpolysiloxane (6 cs) | 20.0 |
| (3) Polyoxyalkylene modified organopolysiloxane | 2.8 |
| (4) Carnauba wax | 8.0 |
| (5) Aristo wax (165° F.) | 8.0 |
| (6) Diglyceryl dioleate | 3.0 |
| (7) Dextrin fatty acid ester treated iron oxide red* | 0.3 |
| (8) Silicone treated iron oxide yellow* | 1.0 |
| (9) Red #204 | 0.7 |
| (10) Dibutylhydroxy toluene | q.s. |
| (11) Flavor | q.s. |
| (12) Deionized water | balance |
| (13) Atelocolagen | 0.3 |
| (14) Sodium pyrrolidone carboxylate | 0.5 |
| (15) Preservative | q.s. |

*Treated in the same manner as mentioned above

Example 31

Lip Treatment

| Ingredient | % |
| --- | --- |
| (1) Squalane | 10.0 |
| (2) Lanolin | 2.0 |
| (3) Octamethylcyclotetrasiloxane | 10.0 |
| (4) Isoparaffin (b.p. = 155° C.) | 27.0 |
| (5) Trimethylsiloxy silicate | 3.0 |
| (6) Aristo wax (165° F.) | 8.0 |
| (7) Diglyceryl diisostearate | 3.0 |
| (8) Silicone treated iron oxide yellow* | 3.0 |
| (9) Silicone treated iron oxide red* | 0.8 |
| (10) Silicone treated finely divided titaium dioxide* | 3.0 |
| (11) Delonized water | balance |
| (12) Glycerol | 5.0 |
| (13) Sodium lactate | 0.3 |
| (14) Sodium l-glutamate | 0.3 |
| (15) Sodium hyaluronate | 0.1 |
| (16) Sorbiol | 0.5 |
| (17) Red #202 | 0.01 |
| (18) Menthol | 0.1 |
| (19) Flavor | q.s. |
| (20) Preservative | q.s. |

*Treated in the same manner as mentioned above.

We claim:

1. A water-in-oil emulsified solid cosmetic composition comprising 5% to 80% by weight of a silicone oil, 3% to 30% by weight of a solid wax, 0.2% to 10% by weight of a polyoxyalkylene modified organopolysiloxane selected from the group consisting of those having the following structures (1), (2), (3), and (4), and 5% to 60% by weight of water, all based on the total amount of the composition:

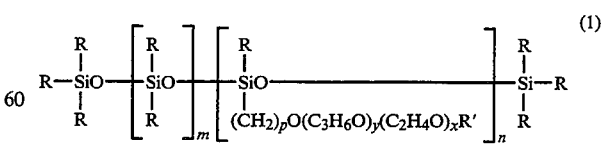

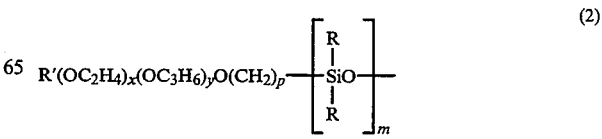

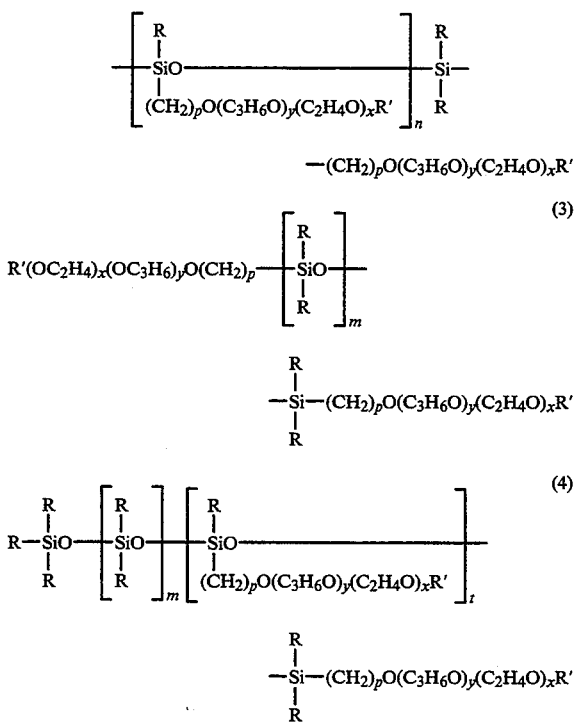

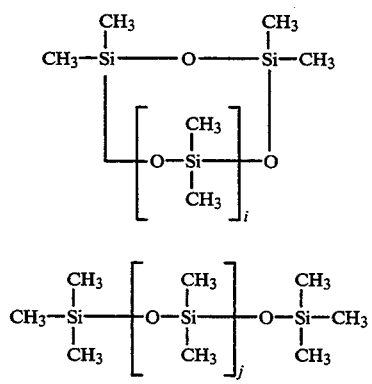

wherein i is an integer of 1 to 6 and j is 0 or an integer of 1 to 3, the amount of the volatile silicone oil being 5% to 80% by weight based on the total amount of the cosmetic composition.

3. A water-in-oil emulsified solid cosmetic composition comprising 5% to 85% by weight of an oil component of which 30% to 100% by weight is a silicone oil, 5% to 20% by weight of an oil-gelling agent, 0.2% to 10% by weight of a polyoxyalkylene modified organopolysiloxane selected from the group consisting of those having the following structures (1), (2), (3), and (4), and 5% to 10% by weight of water, all based on the total amount of the composition:

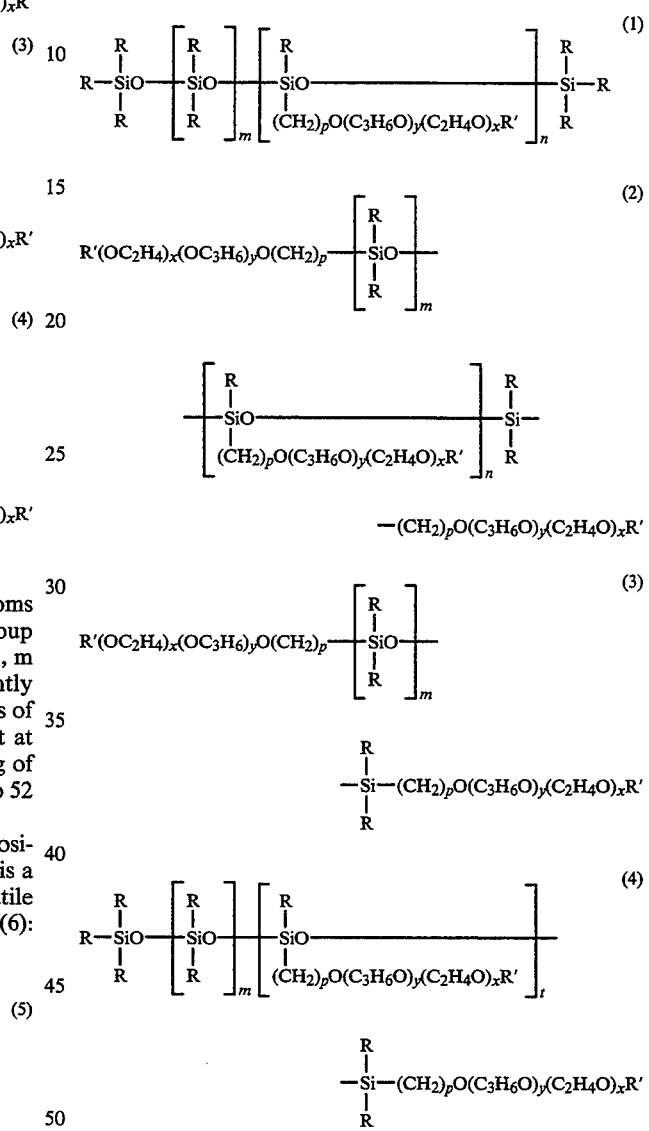

wherein R is an alkyl group having 1 to 3 carbon atoms or a phenyl group, R' is hydrogen or an alkyl group having 1 to 12 carbon atoms, p is an integer of 1 to 5, m is an integer of 5 to 100, n and x are independently integers of 1 to 50, t and y are independently integers of 0 to 50.

4. A water-in-oil emulsified solid cosmetic composition as claimed in claim 3, further comprising 5% to 50% by weight of a cosmetically acceptable powder.

5. A water-in-oil emulsified solid cosmetic composition as claimed in claim 3, wherein said silicone oil is a member selected from the group consisting of volatile silicone oils having the following structures (5) and (6):

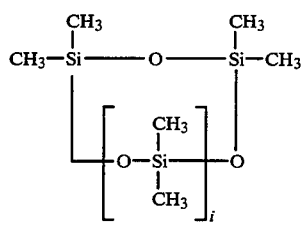

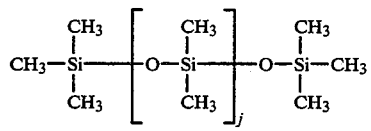

wherein i is an integer of 1 to 6 and j is 0 or an integer of 1 to 3, the volatile silicone oil being in an amount 5% to 80% by weight based on the total amount of the cosmetic composition.

6. A water-in-oil emulsified solid cosmetic composition as claimed in claim 3, wherein the main component of said solid wax is a member selected from the group consisting of linear and branched hydrocarbon waxes having 25 to 52 carbon atoms.

7. A water-in-oil emulsified solid cosmetic composition comprising 5% to 85% by weight of a cosmetically acceptable oil, 5% to 20% by weight of a component selected from the group consisting of solid waxes and oil-gelling agents, 0.2% to 10% by weight of at least one polyoxyalkylene modified organopolysiloxane selected from the group consisting of those having the following structures (1), (2), (3) and (4), 5% to 60% by weight of water, 0.2% to 10% by weight of lipophilic surfactant, and 5% to 50% by weight of a hydrophobically treated powder, all based upon the total amount of the composition:

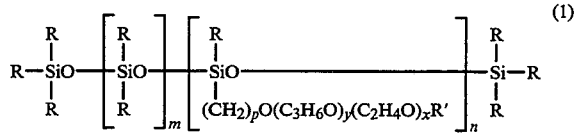

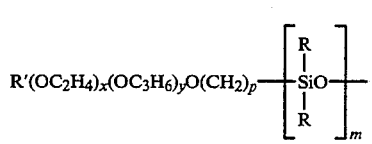

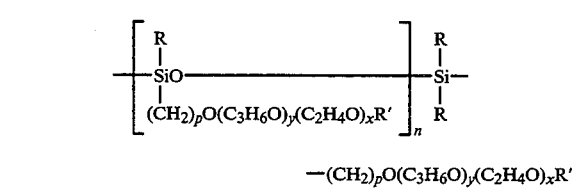

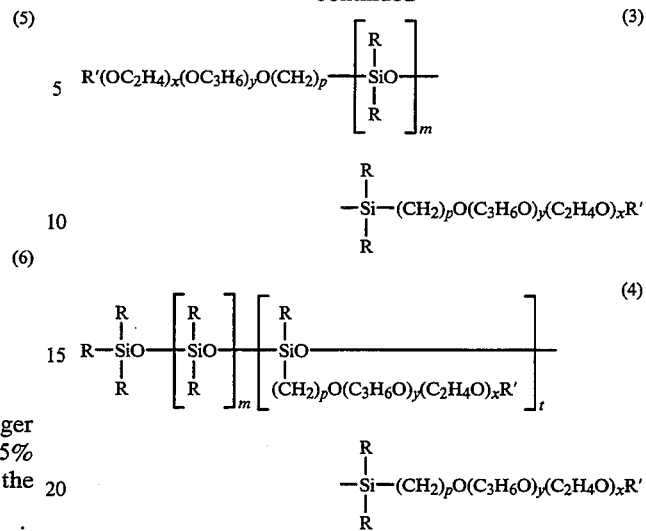

wherein R is an alkyl group having 1 to 3 carbon atoms or a phenyl group, R' is hydrogen or an alkyl group having 1 to 12 carbon atoms, p is an integer of 1 to 5, m is an integer of 5 to 100, n and x are independently integers of 1 to 50, t and y are independently integers of 0 to 50.

8. A water-in-oil emulsified solid cosmetic composition as claimed in claim 7, wherein said cosmetically acceptable oil is a member selected from the group consisting of volatile silicone oils having the following structures (5) and (6):

wherein i is an integer of 1 to 6 and j is 0 or an integer of 1 to 3, the amount of the volatile silicone oil being 5% to 80% by weight based on the total amount of the cosmetic composition.

9. A water-in-oil emulsified solid cosmetic composition as claimed in claim 7, wherein the main component of said solid wax is a member selected from the group consisting of linear and branched hydrocarbon waxes having 25 to 52 carbon atoms.

* * * * *

UNITED STATES PATENT AND TRADEMARK OFFICE
CERTIFICATE OF CORRECTION

PATENT NO. : 5,362,482
DATED : November 8, 1994
INVENTOR(S) : Yoneyama, et al.

It is certified that error appears in the above-indentified patent and that said Letters Patent is hereby corrected as shown below:

Column 25, line 31,   cancel " R" " and substitute --R'--.

Column 26, line 5,    cancel "10%" and substitute --60%--.

Signed and Sealed this

Fifth Day of May, 1998

Attest:

BRUCE LEHMAN

Attesting Officer    Commissioner of Patents and Trademarks